US006225074B1

(12) United States Patent
Wright et al.

(10) Patent No.: US 6,225,074 B1
(45) Date of Patent: May 1, 2001

(54) DIRECT CHLORAMPHENICOL ACETYL TRANSFERASE ASSAY

(76) Inventors: Dennis Wright, 3839 Wiggington Rd., Talahassee, FL (US) 32303; David J. Phelps, 36 Boulder Brook Dr., Stamford, CT (US) 06903

( * ) Notice: Subject to any disclaimer, the term of this patent is extended or adjusted under 35 U.S.C. 154(b) by 0 days.

(21) Appl. No.: 08/932,072

(22) Filed: Sep. 17, 1997

Related U.S. Application Data

(63) Continuation of application No. 08/912,462, filed on Aug. 18, 1997, now abandoned.

(51) Int. Cl.[7] .......................... C12Q 1/48; G01N 33/573; G01N 33/53; C12N 9/10
(52) U.S. Cl. ............................. 435/15; 435/7.4; 435/7.91; 435/193; 435/810
(58) Field of Search .................................. 435/7.4, 7.91, 435/15, 19, 20, 25, 810, 228, 190, 193, 201, 21, 24, 194; 436/826, 904

(56) References Cited

U.S. PATENT DOCUMENTS

| | | |
|---|---|---|
| 4,215,197 | 7/1980 | Tarbutton .............................. 435/18 |
| 4,391,904 * | 7/1983 | Litman et al. ...................... 435/7.91 |
| 4,427,771 | 1/1984 | Misaki et al. .......................... 435/22 |
| 4,613,569 | 9/1986 | Geisler et al. .......................... 435/26 |
| 4,642,295 | 2/1987 | Baker .................................... 436/87 |
| 4,645,742 | 2/1987 | Baker .................................... 436/15 |
| 4,748,111 | 5/1988 | Dattagupta et al. ..................... 435/6 |
| 4,847,194 | 7/1989 | Quante ................................ 435/7.92 |
| 4,847,196 | 7/1989 | Geisler et al. .......................... 435/26 |
| 4,849,347 | 7/1989 | Familletti et al. ...................... 435/26 |
| 4,956,301 | 9/1990 | Ismail et al. .......................... 436/87 |
| 4,978,613 | 12/1990 | Bieniarz et al. ....................... 435/18 |
| 5,037,738 * | 8/1991 | Lamos et al. .......................... 435/12 |
| 5,053,336 | 10/1991 | Vanderlaan et al. ............. 530/388.21 |
| 5,082,780 | 1/1992 | Warren, III et al. ................. 435/191 |
| 5,139,934 | 8/1992 | Stewart et al. ...................... 435/7.92 |
| 5,185,450 * | 2/1993 | Owen .................................. 548/194 |
| 5,188,938 | 2/1993 | Khanna et al. ....................... 435/7.7 |
| 5,206,178 * | 4/1993 | Monji et al. .......................... 436/518 |
| 5,258,295 * | 11/1993 | Starr et al. ......................... 435/172.3 |
| 5,262,545 | 11/1993 | Haughland et al. ................. 548/405 |
| 5,354,658 | 10/1994 | Wright .................................... 435/6 |
| 5,364,764 | 11/1994 | Haughland et al. .................... 435/15 |
| 5,387,515 * | 2/1995 | Bruce et al. .......................... 435/148 |
| 5,627,045 * | 5/1997 | Bochner et al. ........................ 435/34 |
| 5,670,327 | 9/1997 | Wright .................................. 435/7.4 |
| 5,789,179 | 8/1998 | Brophy et al. ......................... 435/7.4 |
| 5,837,458 * | 11/1998 | Minshull et al. ........................ 435/6 |

FOREIGN PATENT DOCUMENTS

| | | |
|---|---|---|
| 58539 * | 8/1982 | (EP) . |
| 08333352 * | 12/1996 | (JP) . |
| 88/08882 * | 11/1988 | (WO) . |
| 90/12318 * | 10/1990 | (WO) . |

OTHER PUBLICATIONS

Young et al., "A Nonradioactive Assay for Transfected Chloramphenicol Acetyltransferase Activity Using Fluorescent Substrates," *Analytical Biochemistry*, 197, 401–407 (1991).
Suto et al., "Selection of an Optimal Reporter Gene for Cell–Based High Throughput Screening Assays," *Journal of Biomolecular Screening*, vol. 2, No. 1 (1997), 7–9.
Kingston et al.., "Uses of Fusion Genes In Mammalian Transfection," *Current Protocols in Molecular Biology*, supplement 12, pp. 9.6.1–9.6.2 (1990).
Kingston et al.., "Reporter System Using Chloramphenicol Acetyltransferase," *Current Protocols in Molecular Biology*, supplement 12, pp. 9.6.3.–9.6.10 (1990).
Brasier, Allan R., "Reporter System Using Firefly Luciferase," *Current Protocols in Molecular Biology*, supplement 12, p. 9.6.11–9.6.15 (1990).
Nenlifesci, "NEN™ Life Science Products: Technical Information," online product information booklet (1998).
Promega, "CAT Enzyme Assay System with Reporter Lysis Buffer", on line product information. (1996), 1–8.
Promega, "Frequently Asked Questions: CAT Enzyme Assay System and pCAT® 3 Vectors", on line product information, (1997), 1–3.
Boehring Mannheim, "Products for Reporter Gene Detection," online product information booklet (1998), 186–187.
"Superior Products for Reporter Gene Analysis," Boehringer Mannheim products information in *Biochemica*, No. 2 (1997).
Sigma–Aldrich, "Chloramphenicol Acetyltransferase (CAT) Reporter Gene Activity Detection," online product information booklet, 1999.
Strategene, "FLASH® CAT Nonradioactive CAT Assay," online product information catalog (1998), 1–2.
Neumann, et al., "A Novel Rapid Assay for Chloramphenicol Acetyltransferease Gene Expression", *Biotechniques* , 5, 444–446, 448 (1987).
Sleigh, M. J., "A Nonchromatographic Assay for Expression of the Chloramphenicol Acetyltransferase Gene in Eucaryotic Cells", 251–257 (1986).

(List continued on next page.)

Primary Examiner—Jon P. Weber
(74) Attorney, Agent, or Firm—Kalow & Springut LLP

(57) ABSTRACT

A direct assay for chloramphenicol acetyl transferase (CAT) has been presented wherein the assay reagent comprises chloramphenicol, an acyl CoA compound, and a tetrazolium salt, and wherein the reagent does not have any added coupling redox enzymes. In one embodiment, the reagent is mixed with the test sample and the presence of CAT is detected by an optical response. In a second embodiment, the reagent is mixed with a test sample containing CAT and the optical response is quantitated by comparison with standards to measure CAT activity in the test sample. In another embodiment, an exogenous electron carrier such as phenazines may be used to enhance the detection of CAT. The assay for the presence or activity of CAT can be used in a high-throughput screening assay or to detect CAT as a reporter gene for measuring the expression of a gene of interest. Kits containing the reagents are also provided.

52 Claims, No Drawings

OTHER PUBLICATIONS

Gendloff, et al., "Quantitation of chloramphenicol acetyl transferase in transgenic tobacco plants by ELISA and correlation with gene copy number", *Plant Molecular Biology*, 14:575–583 (1990).

Tomizawa, J., "Control of Co1E1 Plasmid Replication: Initial Interaction of RNA I and the Primer Transcript is Reversible", *Cell*, 40, 527–535 (1985).

Shaw, W. V, "Chloramphenicol Acetyltransferase from Chloramphenicol–Resistant Bacteria", *Methods in Enzymology*, vol. 43, 737–755 (1975).

Burns et al., "An Immunological Assay for Chloramphenicol Acetyltransferase", *Analytical Biochemistry*, 162, 399–404 (1987).

Kugler, P. Histochemistry 75:99–112 (1982) "Quantitative Dehydrogenase Histochemistry . . . ".

Blake et al., Analytical Biochemistry 136:175–179 (1984) "A Rapid, Sensitive Method for Detection of Alkaline Phosphate–Conjugated . . . ".

Heegaard, Neils H. H., Applied and Theoretical Electrophoresis 1:261–264 (1990) "Visualization of alkaline phophotase by means of formazin staining".

Kiyama et al., Neuroscience Research 9 (1990) pp. 1–21 "Recent progess in the use of the technique of non–radioactive in situ hybridization . . . ".

Boehringer Mannheim Corporation. "Nonradioactive DNA Labeling and Detection Kit" (Nov. 1990).

Bondi, A. et al., Histochemistry, vol. 76, pp 153–158, 1982.

Gossrau, R., Histochemistry, vol. 58, pp 203–218, 1978.

Terazawa, K. et al., J. Immunoassay, vol. 12, No. 2, pp. 277–292, 1991.

Sigma Catalog, 1994, p. 974.*

Oldenburg et al. "A dual culture assay for detection of antimicrobial activity", J. Biomol. Screening (Mar. 1996) 1(3): 123–130 (abstract only).*

Lam et al. "Application of a dual color detection scheme in the screening of a rangom combinatorial peptide library", J. Immunolog. Meth. (1995) 180: 219–23.*

Marshall et al. Growth Regulation (Jun. 1995) 5(2): 69–84.*

Ewing et al. Analytical Biochem. (Dec. 10, 1995) 232(2): 243–8.*

Morris et al. Clin. Chem. (1986) 32(6): 1083–4.*

Hammond et al., "Isolation of Enzymes with Novel Capabilities for Use in Clinical Analysis", Ann. N. Y. Acad. Sci., 542(Enzyme Eng. 9), pp. 502–506, Dec. 1988.*

Hammond et al., "Enzyme–Based Chloramphenicol Estimation", Lancet, II, No. 8556, p. 449, Aug. 1987.*

Morris et al., "Development of an Enzyme Mediated Colorimetric Assay for Chloramphenicol", Clinical Chemistry, 32(6), pp. 1063–1064, 1986.*

* cited by examiner

DIRECT CHLORAMPHENICOL ACETYL TRANSFERASE ASSAY

This application is a continuation of application Ser. No. 08/912,462, filed Aug. 18, 1997 now abandoned.

FIELD OF THE INVENTION

The present invention relates to a method of detection of enzymatic chemical reactions that result in the cleavage or formation of a chemical, usually covalent bond. Most particularly, the invention is a method for the chromogenic or fluorogenic detection of such enzyme reactions, in particular as an assay screen for new chemical combination that are produced by biotechnology methodologies, that may have activity in enzyme-substrate interactions.

1. Background of the Invention

Enzymes are catalytic proteins that are pervasive in biological systems. Many enzymes catalyze specific reactions which entail the cleavage or formation of a chemical bond. In particular such an Enzyme (E) will increase the rate of reaction of a specific Substrate (S) that involves the formation or cleavage of a covalent bond resulting in a Product (P.) Enzymes are necessary in almost every biological reaction, and helpful in many chemical, pharmaceutical and manufacturing processes. Detecting enzyme activity and defining and measuring enzyme-substrate interactions is desirable in many clinical and laboratory situations, particularly in screening enzyme activity and screening molecules as inhibitors, enhancers or modifiers of pharmacologically interesting enzymes.

2. Description of Related Art

Known enzymes are classified by the International Union of Biochemistry Commission on Enzymes into six distinct categories: oxidoreductases, transferases, hydrolases, lyases, isomerases and ligases. Recent advances in enzymology have identified previously unknown and/or non-natural catalytic molecules that have enzymatic-like speed and specificity, such as extremozymes, abzymes, recombinant enzymes, semi-synthetic enzymes, and catalytic ribozymes.

Recently techniques have been developed which permit large numbers of different chemical compounds to be synthesized rapidly and systematically for drug screening. Large collections of such components called, combinatorial chemical libraries, are expensive to produce so that typically only milligram quantities or less of each different molecule is in a library. Screens for different types of pharmacological or chemical activity can generally require different techniques, different instruments, varying time frames, different sensitivity levels, different software and different methods of data interpretation. As a result, to screen a large combinatorial library, or other large collection of compounds for different types of pharmaceutical or chemical activity heretofore required great expenses for training, instrumentation and reagents. Sifting through such libraries of molecules to determine structural features which show activity and act as possible pharmacological or industrial agents is a tremendous effort.

The field of enzyme study dates back more than one hundred years. Many methods to study and detect enzymatic events are now known. Significantly important enzyme-assay methods include: (1) spectophotometry, using either ultraviolet or visual light; (2) fluorometry; (3) assays involving detection of radioactivity; (4) coupled assays; and (5) enzyme linked immunsorbent assays (ELISA.) Virtually every enzyme requires a specific and unique substrate for its reactivity. The development of an assay for a particular enzyme/substrate reaction is often a difficult endeavor. Because this is a mature field—although still the subject of intense research and development activities—many textbooks and compilations of methods exist, in addition to articles in peer-reviewed journals.

Conventional assays for enzyme activity are virtually as numerous as the number of enzymes. Some examples of conventional assays for enzyme activity are:

creatine kinase, which is used as a serum control for the diagnosis of muscle deterioration is most frequently assayed in a coupled system with pyruvate kinase and lactate dehydrogenase;

proteases are conventionally measured using specific synthetic substrates which contain a chromogenic or fluorogenic enzyme conjugate at the amide bond which is hydrolyzed by the enzyme;

chloramphenicol acetyl transferase (CAT) is a widely used reporter gene in expression studies. There are several commercially available assays. Such assays for CAT include enzyme linked assays (ELISA), radioactive assays and fluorescent methods. Conventional ELISA methods for assaying for CAT typically take from 2–4 hours and are generally sensitive to only $1-2.5 \times 10^{-12}$ g/ml of enzyme. The radioactive and fluorescent assays use expensive and/or dangerous reagents, and typically require a time-consuming post-event separation to measure the CAT activity.

Due to ease of use, specificity and sensitivity, the current method of choice for detection is most assay systems is radioactivity. However the rapid decay of the radioactive probe, danger of radiation exposure, extensive processing of samples, and storage and disposal problems for radioactive materials make non-radioactive methods of detection desirable.

For conventional non-radioactive detection systems to work, synthetic substrates must be designed to report on the event being monitored. In the case of many proteases, hydrolysis products serve to report on the activity of the protease. However, such hydrolysis products are frequently carcinogenic.

The design of non-radioactive methods usually involves the attachment of chromophores, fluorophores or lumigens at the scissile bond of the reporter substrate. A signal is generated if the enzymatic event takes place because a detectable chromogenic, fluorogenic or lumigenic species is liberated. Designing such reporter substrates is difficult; when a probe is introduced onto the substrate, the substrate can lose its lock and key fit to the enzyme, thus losing its enzyme specificity. If the substrate still fits the enzyme, the binding and energetics of the enzyme catalysis may be altered in significant ways with the result that the synthetic reporter substrate will not be a true measure of the enzyme reaction.

Proteases are enzymes that hydrolyze proteins. All living organisms contain proteases to metabolize proteins, regulate cellular processes, defend themselves against exogenous proteins and mediate other important requirements of survival. In the purification of any protein from a natural source, it is necessary to inhibit endogenous proteases to prevent them from breaking down the proteins of interest. The search for the presence of known and unknown proteases in a sample is an important endeavor both at the research stage and the development stage in all areas of biotechnology and related sciences. If the protease is known and it is known to be in the sample of interest, methods for its analysis and strategies for its purification or inhibition will generally have been elaborated. If a sample contains a protease which is not known or, which is not known to be present in that sample, it may be difficult to determine that one is even present in that sample and considerably more difficult to determine what type of protease it is in order to inhibit its activity.

Proteases are classified into a number of categories dependent upon their mechanism of action. They are further classified dependent upon the cleavage site in the proteins which they hydrolyze. The combination of action and cleavage site leads to multiplicative complexity in determining what proteases are present and how their activities might be inhibited. There is no single cleavage site in a protein which will be hydrolyzed by all enzymes and therefore no known substrate which will be a reporter for all enzymes. More importantly, there is no rapid, sensitive high-throughput method to characterize many types of enzyme activity in a single experiment.

Existing art is aimed at determining if any protease activity is present in a sample and is limited to two types of tests:

a. Fluorescently labeled casein;
b. Electrophoretic mobility assay.

Each of these assays typically requires lengthy incubation, is therefore slow (the test may take hours). Moreover the assays are generally insensitive, and may require post-hydrolysis separation or expensive instrumentation. In the best of circumstances and either assay will tell if protease activity is present, but cannot tell what type of protease is present, whether there is more than one type of protease present, or how to analyze or inhibit the protease based on known enzyme-substrate interaction.

Tetrazolium salts have been used for the study of the mitochondrial respiratory chain in vivo. A reduction of a substrate by an enzyme produces electrons which are transferred to the tetrazolium salt yielding a formazan which is deeply colored. The tetrazolium salt thus functions as an indication. The use of an exogenous electron carrier such as phenazine methosulfate can significantly increase the speed and sensitivity of the reaction. U.S. Pat. No. 5,354,658 entitled "Non-Radioactive Method for Detecting a Labelled Segment and A Solution or Composition Therefor", the disclosure of which is hereby incorporated by reference, describes a sensitive and specific method of using phenazine methosulfate and dimethylthiazole diphenyl tetrazolium (MTT) to detect a specific enzyme-substrate in particular the reaction of alkaline phosphatase with a 5-bromo-4-chloro-3-indolyl phosphate reaction in vitro. The method of the patent allows a thousand times greater increase of sensitivity, and orders of magnitude greater speed than previously reported tetrazolium methods. However this patent did not address or solve the problem of screening large combinatorial chemical libraries rapidly and efficiently, much less teach or suggest any solution to that problem.

SUMMARY OF THE INVENTION

According to the present invention there is provided a non-radioactive method of monitoring an enzyme-substrate reaction by addition of an exogenous electron carrier and a tetrazolium salt to the reaction medium, and allowing the reaction to proceed to a colored or fluorescent formazan in an irreversible reaction. Preferred tetrazolium salts for the invention have the structure of (1) where R is cyano, aryl, heteroaryl or aralkyl; R1 is aryl, heteroaryl, or aralkyl and R2 is aryl, heteroaryl or aralkyl including: 3-(4,5-dimethylthiazol-2-yl)-2,5-diphenyltetrazolium bromide (MTT); 2,2'-di-p-nitrophenyl-5,5'-diphenyl-3,3'-(3,3'-dimethoxy-4,4'-diphenylene)ditetrazolium chloride (nitroblue tetrazolium, NBT); 2,3,5-triphenyl tetrazolium chloride (TTC); 2-(2'-benzothiazolyl)-5-styryl-3-(4-phthalhydrazidyl) tetrazolium chloride (BPST); neotetrazolium chloride (NTC); 2,3-bis(2-methoxy-4-nitro-5-sulfophenyl)-2-H-tetrazolium-5-carboxanilide inner salt (XTT); p-iodonitrotetrazolium violet (INT) and

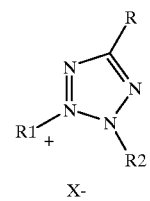

(1)

cyanoditolyl tetrazolium chloride (CTC). Dimers of tetrazolium salts also are useful to this invention. It is anticipated that dimethylthiazol diphenyl tetrazolium (MTT) as the tetrazolium salt will be particularly preferred in this invention.

Preferred exogenous electron carriers for the invention include: phenazine methosulfate (PMS); phenazine ethosulfate (PES), nicotinamide adenine dinucleotide (NAD); nicotinamide adenine dinucleotide; flavin adenine dinucleotide (FAD) or 4-aminoantipyrine.

The tetrazole-catalyst color indicator test can be linked to a wide variety of different enzyme-substrate electron transfers.

The present invention also provides for a solution or composition to be used as a test kit. The test kit of the invention would include a substrate, a tetrazolium salt and an electron carrier which when in solution added to a sample to be assayed would be capable of producing a colored or fluorescent formazan which results in a color or fluorescent change indicative of an electron transfer. Alternatively, the test kit could include one or more substrates, one or more enzymes, one or more cofactors a tetrazolium salt, an electron carrier and one or more specific inhibitors which when in solution added to a sample to be assayed would be capable of producing a colored or fluorescent formazan which results in a color or fluorescent change indicative of an electron transfer.

Preferred embodiments of the invention provide for a chromogenic or fluorogenic method that is non-radioactive and can be amenable to existing instrumentation, and software packages for enzyme analysis. The preferred methods of the invention have considerably high sensitivity, namely a sensitivity of $10^{-15}$ gram or less in contrast to prior methods of $10^{31\ 12}$ i.e. $10^3$ or 1,000 times more sensitive. Moreover, preferred embodiments of the invention can achieve a detectable color change in five to fifteen minutes. No amplification technique of the formazan product is required in preferred embodiments of the invention. No stabilizing agent for the tetrazolium salt is required in preferred embodiments.

The present invention permits different enzymes to be studied using the same spectrophotometer or plate reader, the same robotic system, the same training or personnel, similar or identical reagent systems, similar or identical disposables and consumables, similar or identical software, and similar or identical calculations of activity. Preferred embodiments of the present invention may be used to particular advantage in carrying out screening for useful chemical activities of the compounds of chemical libraries since all screens for various activities of interest using the tetrazolium and electron carrier will deliver the identical detection molecule, with the same wavelength of detection, the same extinction coefficient, similar reaction times and similar sensitivity and detection levels. In addition, with proper planning, the use of inhibitors or other chemicals, will allow the possibility of two or more entirely different screens to be done in the same microwell or cuvette or on the same blot.

The invention described herein has many advantages over the previous methods of detection, including the use of natural substrates, the ability to assay a wide variety of enzymes, presumably even presently unknown enzymes, to detect activity, and the ability to tailor the reaction to a specific determination of one enzyme in the presence of competing enzymatic activities.

DESCRIPTION OF THE PREFERRED EMBODIMENTS

In one preferred embodiment of the invention, enzyme-substrate reactions are detected by transfer of an electron to dimethylthiazol diphenyl tetrazolium bromide. Dimethylthiazol diphenyl tetrazolium bromide has the chemical name of 3-(4,5-dimethylthiazol-2-yl)-2,5-diphenyl-2-H-tetrazolium bromide, the chemical formula, $C_{18}H_{16}N_5SBr$, a molecular weight of 414.33, a melting point of 195°(dec), and an absorption of λMAX 378 nm.

The preferred exogenous electron carrier phenazine methosulfate has the clinical formula of N-methylphenazonium methosulfate, the chemical formula $C_{14}N_{14}N_2O_4S$, a molecular weight of 306.34 and a melting point between 158°–160° (dec), and an absorption at λmax 386 nm.

In a preferred assay of the invention, the enzyme chloramphenicol acetyl transferase (CAT enzyme) reacts with chloramphenicol and actyl CoA in the presence of the indicator dimethylthiazol tetrazolium (MTT) and phenazine methosulfate (PMS). The MTT serves as a hydrogen acceptor in the reaction. The reaction can be written as:

CAT+chloramphenicol+acyl coA→CAT-chloramphenicol-CoA

CAT-chloramphenicol-CoA+PMS→CAT+PMS-$H_2$+acyl-chloramphenicol+HS-CoA

PMS-$H_2$+MTT→formazan+PMS.

The formazan product is colored and may therefore be detected in the presence of the other reaction species, which are generally colorless.

While an assay for chloramphenicol acetyl transferase, ad described above, is a preferred application of the invention the method may be used to detect substantially all categories of enzyme activity; for example, oxidoreductases, transferases, hydrolases, lyases, isomerases, ligases and novel classes of enzymes. Consequently, the enzyme activity assay of the present invention is expected to have applicability in both commercial processes such as pharmaceutical development, insect control, food science, pulp and paper, laundry and other industrial processes and basic molecular scientific research.

In addition, with this invention, test kits for specific enzyme/substrate interactions could be provided that include specific substrates and a tetrazolium dye. Individually, the different substrates would have different special characteristics and therefore could not be detected conventionally by the same spectrophotometer or microplate reader at the same time, same wavelength and same extinction coefficient. In contrast, with the present invention, different substrates ultimately yield the same reduced formazan, so that multiple enzymes can be studied with the same spectroscopic settings. A single microplate could have wells for each specific substrate. Combinations of inhibitors and control enzymes could be used to define new or unexpected enzymatic activities. Observing the development of color would confirm the presence or absence of specific enzymes.

The unique feature of this invention is that widely different enzymes, widely different inhibitors and widely different specific substrates can be studied with the same tetrazolium detection reagent and the same spectrophotometer or plate reader. This adds a tremendous efficiency over current art.

EXAMPLES

The generalized reaction where E=enzyme, S=substrate, T=tetrazolium salt, C=electron carrier, P=product is:

E+S→E-S

E-S+T→E+$TH_2$+P or

E+S→E-S

E-S+C→E+$CH_2$+P $CH_2$+T→C+$TH_2$

The experimental results for Experiments 1–12 are described by the color change of the experimental solution. These colors result from the interaction of the enzyme and substrate with the transfer of an electron to a tetrazolium salt. The reactive product, formazan, is detected as dark blue, black. The BCI substrate without MTT is pale blue. PMS and MTT alone are yellow. PMS and BCI is yellow+blue which is green. The reaction detected required the enzyme, substrate and tetrazolium salt.

Example 1

Microtiter testing was performed, with the following substrate combinations to demonstrate chromogenic detection of esterase (EC3.1.1.1).

Reagents:

| | |
|---|---|
| PBS | Phosphate Buffer Solution |
| MTT | Dimethylthiazol Tetrazolium (Sigma M-2128) |
| PMS | Phenazine methosulfate (Sigma P-9625) |
| BCI acetate | 5-Bromo-4-chloro-3-indolyl acetate (Sigma B-4377) in 50% Dimethyl formamide |
| Esterase | diluted with PBS @ pH 7.4 to a final concentration of 100 units/ml (Sigma E-2884) |

Experiment

Four test samples were prepared. The samples A, B, C, D contained the following reactants:

| | |
|---|---|
| A. | 100 µl PBS (Phosphate Buffer Solution) @ pH 7.4 |
| | 10 µl MTT (10 mM) |
| | 10 µl PMS (10 mM) |
| | 10 µl BCI acetate @ 12.5 mg/ml |
| B. | 100 µl PBS @ pH 7.4 |
| | 10 µl MTT (10 mM) |
| | 10 µl $H_2O$ |
| | 10 µl BCI acetate @ 12.5 mg/ml |
| C. | 100 µl PBS @ pH 7.4 |
| | 10 µl MTT (10 mM) |
| | 10 µl $H_2O$ |

-continued

| | | |
|---|---|---|
| D. | | 10 μl BCI acetate @ 12.5 mg/ml |
| | | 100 μl PBS @ pH 7.4 |
| | | 10 μl MTT (10 mM) |
| | | 10 μl PMS (10 mM) |
| | | 10 μl BCI acetate @ 12.5 mg/ml |

10 μl of $H_2O$ was added to substrate sample A to serve as a control. 10 μl of the enzyme esterase (1 unit) was added to substrate samples B, C, and D. Detection of test results was done by visual determination.

Results

| Sample | Contents | Reaction |
|---|---|---|
| A | MTT, PMS, BCI acetate (no esterase) | yellow - no color change detected |
| B | MTT, $H_2O$, BCI acetate, 10 μl esterase | dark blue < 10 seconds) |
| C | $H_2O$, PMs, BCI acetate, 10 μl esterase | yellow-blue - slight change |
| D | MTT, PMS, BCI acetate, 10 μl esterase | dark blue (instantaneous) |

Example 2

Microtiter testing was performed, with the following substrate combination—in duplicate —to demonstrate chromogenic detection of esterase (EC3.1.1.1):

Reagents:

| | |
|---|---|
| MTT (10 mM) | Dimethylthiazol Tetrazolium (Sigma M-2128) |
| PMS (10 mM) | Phenazine methosulfate (Sigma P-9625) |
| BCI acetate | 5-Bromo-4-chloro-3-indolyl-acetate (Sigma B 4377) in 1 ml of $H_2O$ to a 5 mg/ml concentration |
| BCI butyrate | 5-Bromo-4-chloro-3-indolyl-butyrate (Sigma B 9151) in 1 ml of $H_2O$ to a 5 mg/ml concentration |
| Esterase | Diluted with $H_2O$ to a 5 mg/ml concentration (Sigma E-2884) |

| | | | | |
|---|---|---|---|---|
| A. | 100 μl de-ionized $H_2O$ | A'. | 100 μl de-ionized $H_2O$ | |
| | 10 μl MTT (10 mM) | | 10 μl MTT (10 mM) | |
| | 10 μl PMS (10 mM) | | 10 μl PMS (10 mM) | |
| | 10 μl BCI butyrate | | 10 μl BCI acetate | |
| B. | 100 μl de-ionized $H_2O$ | B'. | 100 μl de-ionized $H_2O$ | |
| | 10 μl MTT (10 mM) | | 10 μl MTT (10 mM) | |
| | 10 μl $H_2O$ | | 10 μl $H_2O$ | |
| | 10 μl BCI butyrate | | 10 μl BCI acetate | |
| C. | 100 μl de-ionized $H_2O$ | C'. | 100 μl de-ionized $H_2O$ | |
| | 10 μl $H_2O$ | | 10 μl $H_2O$ | |
| | 10 μl PMS (10 mM) | | 10 μl PMS (10 mM) | |
| | 10 μl BCI butyrate | | 10 μl BCI acetate | |
| D. | 100 μl de-ionized $H_2O$ | D'. | 100 μl de-ionized $H_2O$ | |
| | 10 μl MTT (10 mM) | | 10 μl MTT (10 mM | |
| | 10 μl PMS (10 mM) | | 10 μl PMS (10 mM) | |
| | 10 μl BCI butyrate | | 10 μl BCI acetate | |
| E. | 120 μl de-ionized $H_2O$ | E'. | 120 μl de-ionized $H_2O$ | |
| | 10 μl BCI butyrate | | 10 μl BCI acetate | |

10 ul of $H_2O$ was added to substrate sample A and A' to serve as a control. 10 ul of esterase (1 unit) was added to substrate samples B, B', C, C', D, D', and E, E'.

| Sample | Contents | Reaction |
|---|---|---|
| A | MTT, PMS, BCI-butyrate (no esterase) | yellow - no color change detected |
| B | MTT, $H_2O$, BCI-butyrate (esterase) | dark blue (<30 minutes) |
| C | $H_2O$, PMS, BCI-butyrate (esterase) | yellow-blue (<30 minutes) |
| D | MTT, PMS, BCI-butyrate (esterase) | dark blue (<20 minutes) |
| E | BCI-butyrate (ester) | pale blue (>1 hour) |
| A' | MTT, PMS, BCI-acetate (no esterase) | yellow - no color change dected |
| B' | MTT, $H_2O$, BCI-acetate (esterase) | dark blue (<10 sec) |
| C' | $H_2O$, PMS, BCI-acetate (esterase) | yellow-blue (<30 sec) |
| D' | MTT, PMS, BCI-acetate (esterase) | dark blue (instant detection) |
| E' | BCI-acetate (esterase) | pale blue (>10 minutes) |

All chromogenic BCI-butyrate reactions were observed to be much slower than the corresponding BCI-acetate reactions, event though the concentration of substrates and enzymes were similar. This indicates that the acetate reactions are a better substrate for esterase. Time to react could be used to qualify different substrates in unknown samples.

Example 3

Microtiter testing was performed, with the following substrate combinations to demonstrate chromogenic detection of esterase (EC3.1.1.1).

Reagents:

| | |
|---|---|
| MTT (10 mM) | Dimethylthiazol Tetrazolium (Sigma M-2128) |
| PMS (10 mM) | Phenazine methosulfate (Sigma P-9625) |
| BCI acetate | 5-Bromo-4-chloro-3-indolyl 1,3 diacetate (Sigma B-5630) in $H_2O$ (5 mg/ml) |
| Esterase | diluted with $H_2O$ to a final concentration of 100 units/ml (Sigma E-2884) |

Experiment

Five test samples were prepared. The samples A, B, C, D, E contained the following reactants:

| | |
|---|---|
| A. | 100 μl de-ionized $H_2O$ |
| | 10 μl MTT (10 mM) |
| | 10 μl PMS (10 mM) |
| | 10 μl BCI-1,3 diacetate |
| B. | 100 μl de-ionized $H_2O$ |
| | 10 μl MTT (10 mM) |
| | 10 μl $H_2O$ |
| | 10 μl BCI-1,3 diacetate |
| C. | 100 μl de-ionized $H_2O$ |
| | 10 μl PMS (10 mM) |
| | 10 μl $H_2O$ |
| | 10 μl BCI-1,3 diacetate |
| D. | 100 μl de-ionized $H_2O$ |
| | 10 μl MTT (10 mM) |
| | 10 μl PMS (10 mM) |
| | 10 μl BCI-1,3 diacetate |
| E. | 120 μl de-ionized $H_2O$ |
| | 10 μl BCI-1,3 diacetate |

10 μl of $H_2O$ was added to substrate sample A to serve as a control. 10 μl of the enzyme esterase (1 unit) was added to substrate samples B, C, D and E. Detection of test results were done by visual determination.

Results

| Sample | Contents | Reaction |
|---|---|---|
| A | MTT, PMS, BCI-1,2 diacetate (no esterase) | yellow - no color change detected |
| B | MTT, H$_2$O, BCI-1,3 diacetate, 10 µl esterase | dark blue (>1 hour) |
| C | H$_2$O, PMS, BCI-1,3 diacetate, 10 µl esterase | yellow-blue |
| D | MTT, PMS, BCI-1,3 diacetate, 10 µl esterase | dark blue (>40 minutes) |
| E | H$_2$O, BCI-1,3 diacetate | pale faint blue |

All chromogenic BCI-1,3 diacetate reactions were observed to be much slower than the corresponding BCI-acetate and slower than the BCI-butyrate reactions. Of the BCI-substrates tested, substrate, preference for both esterase and cholesterol esterase is BCI-acetate>BCI-butyrate>BCI-1,3 diacetate, the concentration of substrates and enzymes were similar. Using a series of substrates which are good, better and best for a set of enzymes, it is possible to distinguish relative activity or presence of one or more enzymes.

Example 4

Microtiter testing was performed, with the following substrate combinations to demonstrate chromogenic detection of B-glucuoronidase (EC3.2.1.3.1).

Reagents:

| | |
|---|---|
| PBS | Phosphate Buffer Solution as aqueous solvent and to maintain pH in the 5.0 range |
| MTT | Dimethylthiazol Tetrazolium (Sigma M-2128) |
| PMS | Phenazine methosulfate (Sigma P-9625) |
| BCI glucuronide | 5-Bromo-4-chloro-3-indolyl-B-D-glucuronide (Sigma B-5285) Reconstituted with 1 ml H$_2$O to a final concentration of 10 mg/ml |
| Beta glucuronidase | Reconstituted with 1 ml H$_2$O to a final concentration of 0.1 unit/µl (Sigma G-5897) |

Experiment

Four test samples were prepared. The samples A, B, C, D contained the following reactants.

| | |
|---|---|
| A. | 100 µl PBS (Phosphate Buffer Solution) @ pH 5.0 |
| | 10 µl MTT (10 mM) |
| | 10 µl PMS (10 mM) |
| | 10 µl BCI glucuronide |
| B. | 100 µl PBS @ pH 5.0 |
| | 10 µl MTT (10 mM) |
| | 10 µl H$_2$O |
| | 10 µl BCI glucuronide |
| C. | 100 µl PBS @ pH 5.0 |
| | 10 µl MTT (10 mM) |
| | 10 µl H$_2$O |
| | 10 µl BCI glucuronide |
| D. | 100 µl PBS @ pH 5.0 |
| | 10 µl MTT (10 mM) |
| | 10 µl PMS (10 mM) |
| | 10 µl BCI glucuronide |
| E. | 100 µl PBS @ pH 5.0 |
| | 10 µl H$_2$O |
| | 10 µl BCI glucuronide |

10 µl of H$_2$O was added to substrate sample A to serve as a control. 10 ul of β-glucuronidase (10 units) was added to substrate samples B, C, and D.

| Sample | Contents | Reaction |
|---|---|---|
| A | MTT, PMS, BCI glucuronide (no glucuronidase) | yellow - no color change detected |
| B | MTT, H$_2$O, BCI glucuronide (glucuronidase) | dark blue (< 5 minutes) |
| C | H$_2$O, PMs, BCI glucuronide (glucuronidase) | yellow-blue - slight change |
| D | MTT, PMS, BCI glucuronide (glucuronidase) | dark blue (<5 minutes) |
| E | H$_2$O, BCI glucuronide (glucuronidase) | pale blue (after 5 minutes) |

Example 5

Microtiter testing was performed with a protease inhibitor and various substrate combinations to demonstrate esterase activity and/or contamination in a commercially available elastase (EC3.4.21.36) preparation.

The esterase substrates were observed to generate positive signal upon addition of an elastase dilution (10 µl). Elastase was serially diluted two fold to signal extinction with elastase substrate. The last dilution yielding robust signal was incubated with the competitive inhibitor elastatinal for 10 minutes—with subsequent addition of esterase substrates.

Reagents:

| | |
|---|---|
| PBS | Phosphate Buffer Solution |
| MTT | Dimethylthiazol Tetrazolium (Sigma M-2128) |
| PMS | Phenazine methosulfate (Sigma P-9625) |
| BCI acetate | 5-Bromo-4-chloro-3-indolyl acetate (Sigma B-4377) in 50% Dimethyl formamide |
| Elastase | (Sigma lot #17H8005) |
| Elastase Substrate | N-Succinyl-ALA-ALA-ALA p nitroanilide in 50% Dimethy formamide (Sigma-4760) 50% DMF at a 12.5 mg/ml concentration |
| Elastatinal | Elasatase inhibitor (Sigma E-0881 |

Results

| Enzyme + | Contents | Reaction |
|---|---|---|
| Elastase + Inhibitor | MTT, PMS, BCI-acetate | dark blue (<5 minutes) |
| Elastase + Inhibitor | Elastase substrate | clear (no color > 10 min.) |
| Elastase + H$_2$O | MTT, PMS, BCI-acetate | dark blue (<5 minutes) |
| Elastase + H$_2$O | Elastase substrate | yellow |

The generation of positive signal with esterase substrates and generation of positive signal in the microtiter wells containing elastase with elastase substrate and no initial signal development in wells containing the elastase—inhibitor reacted with elastase substrate demonstrate the presence of esterase activity and/or contamination in the elastase preparation.

Example 6

Microtiter testing was performed, with the following substrate combinations—in duplicate—to demonstrate chromogenic detection of beta-glucosidase (EC3.2.1.21):

Reagents:

| | |
|---|---|
| MTT (10 mM) | Dimethylthiazol Tetrazolium (Sigma M-2128) |
| PMS (10 mM) | Phenazine methosulfate (Sigma P-9625) |
| BCI glucoside | 5-Bromo-4-chloro-3-indolyl-B-D-glucoside (Sigma M-4527) in 1 ml of H$_2$O to a final concentration of 5 mg/ml |
| Beta glucosidase | Diluted with 10 ml of H$_2$O to a final concentration of 50 units/ml (Sigma lot #37H4031) |

Five test samples were prepared. The samples A, B, C, D, E contained the following reactants:

Experiment:

| | |
|---|---|
| A. | 100 µl de-ionized H$_2$O<br>10 µl MTT (10 mM)<br>10 µl PMS (10 mM)<br>10 µl BCI glucoside @ 5 mg/ml |
| B. | 100 µl de-ionized H$_2$O<br>10 µl MTT (10 mM)<br>10 µl H$_2$O<br>10 µl BCI glucoside @ 5 mg/ml |
| C. | 100 µl de-ionized H$_2$O<br>10 µl H$_2$O<br>10 µl PMS(10 mM)<br>10 BCI glucoside @ 5 mg/ml |
| D. | 100 µl de-ionized H$_2$O<br>10 µl MTT (10 mM)<br>10 µl PMS (10 mM)<br>10 µl BCI glucoside @ 5 mg/ml |
| E. | 120 µl de-ionized H$_2$O<br>10 µl BCI glucoside @ 5 mg/ml |

10 µl of H$_2$O was added to substrate sample A to serve as a control. 10 µl of β-glucosidase (0.5 units) was added to substrate samples B, C, D and E.

| Sample | Contents | Reaction |
|---|---|---|
| A | MTT, PMS, BCI-glucoside (no glucosidase) | yellow - no color change detected |
| B | MTT, H$_2$O, BCI-glucoside (glucosidase) | dark blue (<5 minutes) |
| C | H$_2$O, PMS, BCI-glucoside (glucosidase) | yellow-blue - slight change |
| D | MTT, PMS, BCI-glucoside | dark blue (<5 minutes) |
| E | BCI-glucoside (glucosidase) | pale blue (>10 minutes) |

The presence of enzyme and substrate was rapidly detected, with or without the electron transport carrier PMS.

Blot testing on 0.2 um nitrocellulose membrane was performed to demonstrate chromogenic detection of beta glucosidase, 5 ul of glucosidase (0.25 U) was spotted and allowed to dry. 10 ul of each substrate combination (B, C, D, and E) was applied to the dried enzyme spots. Similar detection results were obtained as above. Controls were tested with 5 ul H$_2$O spots- instead of enzyme- with respective substrate combinations (10 ul)—with no observable detection reaction.

Example 7

Microtiter testing was performed, with identical protocol and substrate combinations of example 5 (in duplicate) to demonstrate chromogenic detection of cholesterol esterase (EC3.1.1.13).

Reagents:

| | |
|---|---|
| MTT (10 mM) | Dimethylthiazol Tetrazolium (Sigma M-2128) |
| PMS (10 mM) | Phenazine methosulfate (Sigma P-9635) |
| BCI acetate | 5-Bromo-4-chloro-3-indoyl-B-D-acetate (Sigma B 4377) in 1 ml of H$_2$O |
| BCI butyrate | 5-Bromo-4-chloro-3-indoyl-B-D-butyrate (Sigma B 9151) in 1 ml of H$_2$O to a 5 mg/ml concentration |
| Cholestrol esterase | reconstituted to a concentration of 5 U/ml with H$_2$O (Sigma C-5921) |

Experiment

10 µl of H$_2$O was added to substrate sample A to serve as a control. 10 ul of cholesterol oxidase (25 U/mL) was added in appropriate testing.

| | | | | |
|---|---|---|---|---|
| A. | 100 µl de-ionized H$_2$O<br>10 µl MTT (10 mM)<br>10 µl PMS(10 mM)<br>10 µl BCI butyrate | A'. | 100 µl de-ionized H$_2$O<br>10 µl MTT (10 mM)<br>10 µl PMS (10 mM)<br>10 µl BCI acetate | |
| B. | 100 µl de-ionized H$_2$O<br>10 µl MTT (10 mM)<br>10 µl H$_2$O<br>10 µl BCI butyrate | B'. | 100 ul de-ionized H$_2$O<br>10 µl MTT (10 mM)<br>10 µl H$_2$O<br>10 µl BCI acetate | |
| C. | 100 µl de-ionized H$_2$O<br>10 µl H$_2$O<br>10 µl PMS (10 mM)<br>10 µl BCI butyrate | C'. | 100 µl de-ionized H$_2$O<br>10 µl H$_2$O<br>10 µl PMS (10 mM)<br>10 µl BCI acetate | |
| D. | 100 µl de-ionized H$_2$O<br>10 µl MTT (10 mM)<br>10 µl PMS (10 mM)<br>10 µl BCI butyrate | D'. | 100 µl de-ionized H$_2$O<br>10 µl MTT (10 mM<br>10 µl PMS (10 mM)<br>10 µl BCI acetate | |
| E. | 120 µl de-ionized H$_2$O<br>10 µl BCI butyrate | E'. | 120 µl de-ionized H$_2$O<br>10 µl BCI acetate | |

10 µl of H$_2$O was added to substrate sample A and A' to serve as controls. 10 ul of esterase (1 unit) was added to substrate samples B, B', C, C', D, D', and E, E'.

| Sample | Contents | Reaction |
|---|---|---|
| A | MTT, PMS, BCI-butyrate (no cholesterol esterase) | yellow - no color change detected |
| B | MTT, H$_2$O, BCI-butyrate (cholesterol esterase (0.05 U)) | dark blue (<30 minutes) |
| C | H$_2$O, PMS, BCI-butyrate (cholesterol esterase (0.05 U)) | yellow-blue - (<30 minutes) |
| D | MTT, PMS, BCI-butyrate (cholesterol esterase (0.05 U)) | dark blue (<20 minutes) |
| E | BCI-butyrate (cholesterol esterase (0.05 U)) | pale blue (>1 hour) |
| A' | MTT, PMS, BCI-acetate (no cholesterol esterase) | yellow - no color change detected |
| B' | MTT, H$_2$O, BCI-acetate (cholesterol esterase (0.05 U) | dark blue (<10 sec) |
| C' | H$_2$O, PMS, BCI-acetate (cholesterol esterase (0.05 U) | yellow-blue (<30 sec) |
| D' | MTT, PMS, BCI-acetate (cholesterol esterase (0.05 U) | dark blue (instant detection) |
| E' | BCI-acetate (cholesterol esterase (0.05 U) | pale blue (>10 minutes) |

All chromogenic BCI-butyrate reactions were observed to be much slower than the corresponding BCI-acetate reactions, event though the concentration of substrates and enzymes were similar. This indicates that the acetate reactions are a better substrate for esterase. Time to react could be used to qualify different substrates in unknown samples.

Example 8

Microtiter testing was performed, with the following substrate combinations—in duplicate —to demonstrate chromogenic detection of cholesterol oxidase (EC1.1.3.6):

Reagents:

| | |
|---|---|
| MTT (10 mM) | Dimethylthiazol Tetrazolium (Sigma M-66H5033) |
| PMS (10 mM) | Phenazine methosulfate (Sigma P-9625) |
| cholesterol oxidase | reconstituted with deionized $H_2O$ to a concentration of 25 U/ml (Sigma C-5421) |
| Cholesterol Std | reconstituted with deionized $H_2O$ to a concentration (Sigma C-9908) 50 mg/dl |

Experiment:

| | |
|---|---|
| A. | 100 µl de-ionized $H_2O$ |
| | 10 µl MTT (10 mM) |
| | 10 µl PMS (10 mM) |
| | 10 µl Cholesterol Std @ 50 mg/dl |
| B. | 100 µl de-ionized $H_2O$ |
| | 10 µl MTT (10 mM) |
| | 10 µl $H_2O$ |
| | 10 µl Cholesterol Std @ 50 mg/dl |
| C. | 100 µl de-ionized $H_2O$ |
| | 10 µl $H_2O$ |
| | 10 µl PMS (10 mM) |
| | 10 µl Cholesterol Std @ 50 mg/dl |
| D. | 100 µl de-ionized $H_2O$ |
| | 10 µl MTT (10 mM) |
| | 10 µl PMS (10 mM) |
| | 10 µl Cholesterol Std @ 50 mg/dl |
| E. | 120 µl de-ionized $H_2O$ |
| | 10 µl Cholesterol Std @ 50 mg/dl |

10 µl of $H_2O$ was added to substrate sample A (substrate control.) Cholesterol Oxidase (25 U/ml) was added to A, B, C, D and E.

Results

| Sample | Contents | Reaction |
|---|---|---|
| A | MTT, PMS, cholesterol (no Cholesterol Oxidase) | yellow, then slight green-yellow |
| B | MTT, $H_2O$, cholesterol (Cholesterol Oxidase) | yellow, no color change |
| C | $H_2O$, PMS, cholesterol (Cholesterol Oxidase) | yellow, no color change |
| D | MTT, PMS, cholesterol (Cholesterol Oxidase) | dark blue (<1 minutes) |
| E | $H_2O$ (Cholesterol Oxidase) | clear, no color change |

Example 9

Microtiter testing was performed with the following substrate combinations in duplicate to demonstrate chromogenic detection of glucose oxidase (EC1.1.3.4):

Reagents:

| | |
|---|---|
| MTT (10 mM) | Dimethylthiazol Tetrazolium (Sigma M-66H5033) |
| PMS (10 mM) | Phenazine methosulfate (Sigma P-9625) |
| glucose oxidase | diluted with $H_2O$ to a concentration of 0.2 U/µl (Sigma G-9010) |
| glucose | solubilized with $H_2O$ to a concentration (Sigma G-8270) 50 mg/ml |

Experiment:

| | |
|---|---|
| A. | 100 µl de-ionized $H_2O$ |
| | 10 µl MTT (10 mM) |
| | 10 µl PMS (10 mM) |
| | 10 µl 5% glucose solution |
| B. | 100 µl de-ionized $H_2O$ |
| | 10 µl MTT (10 mM) |
| | 10 µl $H_2O$ |
| | 10 µl 5% glucose solution |
| C. | 100 µl de-ionized $H_2O$ |
| | 10 µl $H_2O$ |
| | 10 µl PMS (10 mM) |
| | 10 µl 5% glucose solution |
| D. | 100 µl de-ionized $H_2O$ |
| | 10 µl MTT (10 mM) |
| | 10 µl PMS (10 mM) |
| | 10 µl 5% glucose solution |
| E. | 120 µl de-ionized $H_2O$ |
| | 10 µl 5% glucose solution |

10 µl of $H_2O$ was added to substrate sample A as the control sample. Glucose oxidase (2U) was added to samples B, C, D.

Results:

| Sample | Contents | Reaction |
|---|---|---|
| A | MTT, PMS, glucose (no glucose oxidase) | yellow, |
| B | MTT, $H_2O$, glucose (glucose oxidase) | dark blue (>10 min) |
| C | $H_2O$, PMS, glucose (glucose oxidase) | yellow-green |
| D | MTT, PMS, glucose (glucose oxidase) | dark blue (immediate) |

EXAMPLE 10

Microtitre testing was performed with the following substrate combinations in duplicate to demonstrate chromogenic detection of chloramphenicol acetyltransferase (EC 2.3.1.28)

Reagents:

| | |
|---|---|
| MTT (10 mM) | Dimethylthiazol Tetrazolium (Sigma M-66H5033) |
| PMS (10 mM) | Phenazine methosulfate (Sigma P-9625) |
| Chloramphenicol Acetyltransferase | reconstituted with deionized $H_2O$ to a concentration of 500 U/ml (Sigma C-2900) |
| Acetyl CoA | solubilized with deionized $H_2O$ to a concentration of 2 mg/ml |

| Experiment: | |
|---|---|
| A. | 100 μl de-ionized H₂O |
| | 10 μl MTT (10 mM) |
| | 10 μl PMS (10 mM) |
| | 10 μl Acetyl CoA |
| | 10 μl Chloramphenicol |
| B. | 100 μl de-ionized H₂O |
| | 10 μl MTT (10 mM) |
| | 10 μl H₂O |
| | 10 μl Acetyl CoA |
| | 10 μl Chloramphenicol |
| C. | 100 μl de-ionized H₂O |
| | 10 μl H₂O |
| | 10 μl PMS (10 mM) |
| | 10 μl Acetyl CoA |
| | 10 μl Chloramphenicol |
| D. | 100 μl de-ionized H₂O |
| | 10 μl MTT (10 mM) |
| | 10 μl PMS (10 mM) |
| | 10 μl Acetyl CoA |
| | 10 μl Chloramphenicol |

10 μl of H₂O was added to substrate sample A as the substrate control. Chloramphenicol acetyl transferase (5U/10μl) was added to each substrate combination.

Results:

| Sample | Contents | Reaction |
|---|---|---|
| A | MTT, PMS, Chloramphenicol, Acetyl CoA (no Chloramphenicol acetyl transferase) | yellow |
| B | MTT, H₂O, Chloramphenicol, Acetyl CoA (Chloramphenicol acetyl transferase) | orange detection (>5 minutes) |
| C | H₂O, PMS, Chloramphenicol, Acetyl CoA (Chloramphenicol acetyl transferase) | orange (>5 minutes) |
| D | MTT, PMS, Chloramphenicol, Acetyl CoA (Chloramphenicol acetyl transferase) | orange-red (<2 minutes |

Further testing was performed with ten-fold dilutions of the enzyme using substrate sample D. The reaction is sensitive to between 0.5U and 0.05U of enzyme.

EXAMPLE 11

Microtitre testing was performed with the following substrate combinations in duplicate to demonstrate chromogenic detection of neuraminidase (EC 3.2.1.18)

| Reagents: | |
|---|---|
| MTT (10 mM) | Dimethylthiazxol Tetrazolium (Sigma M-66H5033) |
| PMS (10 mM) | Phenazine methosulfate (Sigma P-9625) |
| BCI-acetyl-neuraminic acid | 5-bromo-4-chloro-3-indolyl acetyl neuraminic acid diluted with 500 μl of H₂O |
| Neuraminidase | Solubilized with 1 ml of H₂O to a final concentration of 10 units/ml |

| Experiment: | |
|---|---|
| A. | 100 μl de-ionized H₂O |
| | 10 μl MTT (10 mM) |
| | 10 μl PMS (10 mM) |
| | 10 μl BCI-acetylneuraminic acid |
| B. | 100 μl de-ionized H₂O |
| | 10 μl MTT (10 mM) |
| | 10 μl H₂O |
| | 10 μl BCI-acetylneuraminic acid |
| C. | 100 μl de-ionized H₂O |
| | 10 μl H₂O |
| | 10 μl PMS (10 mM) |
| | 10 μl BCI-acetylneuraminic acid |
| D. | 100 μl de-ionized H₂O |
| | 10 μl MTT (10 mM) |
| | 10 μl PMS (10 mM) |
| | 10 μl BCI-acetylneuraminic acid |
| E. | 120 μl de-ionized H₂O |
| | 10 μl BCI-acetylneuraminic acid |

10 μl of H₂O was added to substrate sample A as the substrate control. 10 μl of neuraminidase (0.1 units) was added to substrate samples B, C, D, and E.

Results:

| Sample | Contents | Reaction |
|---|---|---|
| A | MTT, PMS, BCI-acetylneuraminic acid (no neuraminidase) | yellow |
| B | MTT, H₂O, BCI-acetylneuraminic acid, neuraminidase | light blue formazan reaction |
| C | H₂O, PMS, BCI-acetylneuraminic acid, neuraminidase | green |
| D | MTT, PMS, BCI-acetylneuraminic acid (neuraminidase) | dark blue (>5 minutes) |
| E | H₂O BCI-acetylneuraminic acid (neuraminidase) | pale blue (<2 minutes) |

The presence of enzyme and substrate was rapidly detected with the tetrazolium salt plus the electron transport carrier.

EXAMPLE 12

Microtitre testing was performed with the following substrate combinations in duplicate to demonstrate chromogenic detection of Beta-N-acetylglucosaminidase (EC 3.2.1.30):

| Reagents: | |
|---|---|
| MTT (10 mM) | Dimethylthiazxol Tetrazolium (Sigma M-66H5033) |
| PMS (10 mM) | Phenazine methosulfate (Sigma P-9625) |
| Beta-N-acetylglucoaminidase | solubilized with H₂O (12.5 U/ml) (Sigma A-2415) |
| BCI-acetylglucosaminide | solubilized with 2 ml H₂O to a concentration 12.5 mg/ml (Sigma B-3041) |

| Experiment: | |
|---|---|
| A. | 100 μl de-ionized H$_2$O |
| | 10 μl MTT (10 mM) |
| | 10 μl PMS (10 mM) |
| | 10 μl BCI-acetylglucosaminide |
| B. | 100 μl de-ionized H$_2$O |
| | 10 μl MTT (10 mM) |
| | 10 μl H$_2$O |
| | 10 μl BCI-acetylglucosaminide |
| C. | 100 μl de-ionized H$_2$O |
| | 10 μl H$_2$O |
| | 10 μl PMS (10 mM) |
| | 10 μl BCI-acetylglucosaminide |
| D. | 100 μl de-ionized H$_2$O |
| | 10 μl MTT (10 mM) |
| | 10 μl PMS (10 mM) |
| | 10 μl BCI-acetylglucosaminide |
| E. | 120 μl de-ionized H$_2$O |
| | 10 μl BCI-acetylglucosaminide |

10 μl of H$_2$O was added to substrate sample A (substrate control.) 10 μl Beta-N-acetylglucoaminidase (0.125 units) was added to A, B, C, D and E.

Results:

| Sample | Contents | Reaction |
|---|---|---|
| A | MTT, PMS, BCI-acetylglucosaminide (no Beta-N-acetylglucosaminidase) | yellow |
| B | MTT, H$_2$O, BCI-acetylglucosaminide, Beta-N-acetylglucosaminidase | light blue formazan reaction |
| C | H$_2$O, PMS, BCI-acetylglucosaminide, Beta-N-acetylglucosaminidase | green |
| D | MTT, PMS, BCI-acetylglucosaminide (Beta-N-acetylglucosaminidase) | dark blue (<2 minutes) |
| E | H$_2$O BCI-acetylglucosaminide (Beta-N-acetylglucoaminidase) | light blue (>5 minutes) |

The presence of the enzyme and substrate was rapidly detected in the presence of PMS and MTT.

There are a wide variety of enzymes and inhibitors that can be used with this invention. The following are several examples of possible embodiments:

EXAMPLE 13

Reagents:
X=Substrate+MTT+PMS
E=sample to be analyzed for enzyme activity
I1=TLCK—specific inhibitor for chymotrypsin.
I2=TPCK—specific inhibitor for trypsin
I3=Elastinal—specific inhibitor of elastase
Experiments:

1. E would be incubated with I1, then treated with X: a color should develop if protease other than trypsin present.

2. E would be incubated with I2, then treated with X: a color should develop if protease other than chymotrypsin present.

3. E would be incubated with I3, then treated with X: a color should develop if protease other than elastase present.

4. E would be incubated with I1 and I2, then treated with X: a color if protease other than trypsin or chymotrypsin are present.

5. E would be incubated with I1 and I3, then treated with X: a color should develop if protease other than trypsin or elastase are present.

6. E would be incubated with I2 and I3, then treated with X: a color should develop if protease other than chymotrypsin or elastase are present.

In order to confirm these inhibition-based results, it is possible with this invention to make specific substrate solutions in which MTT and PMS are added to individual solutions of I1, I2 and I3 as defined above. These three different substrates have different spectral characteristics and cannot be read by the same spectrophotometer at the same time at the same wavelength and using the same extinction coefficient to calculate enzymatic activity. With this invention a single microplate could have wells for each inhibition study outlined above and each specific substrate as well. Observing the development of patterns of color would have confirmatory results on identification of the specific enzymes mentioned.

EXAMPLE 14

For lipase enzyme detection on a blot assay, the blot could be impregnated with a solution of the enzyme. Allow to dry. Treat the blot with a solution of natural or synthetic glyceride or cholesteryl ester, plus MTT, plus PMS. A color indicative of enzymatic activity should develop.

EXAMPLE 15

For lipase enzyme detection in solution (microplate, tubes or cuvettes), add an enzyme solution or enzyme-antibody conjugate in solution to each microplate, tubes or cuvettes. Add a solution synthetic or natural glyceride or cholesteryl ester, plus MTT, plus PMS. A color indicative of enzymatic activity develops and could be read in a spectrophotometer or plate reader.

EXAMPLE 16

For the study of lipase inhibition in solution, preincubate the enzyme solution with a solution of inhibitor. Add the substrate solution containing synthetic or natural glyceride or cholesteryl ester, MTT and PMS. Observe the development of color kinetically in comparison to a blank solution which contains enzyme and substrate but no inhibitor.

EXAMPLE 17

For aldolase enzyme detection on a blot assay, the blot could be impregnated with a solution of the enzyme. Allow to dry. Treat the blot with a solution of D-fructose-1,6-biphosphate, plus MTT, plus PMS. A color indicative of enzymatic activity develops.

EXAMPLE 18

For aldolase enzyme detection in solution (microplate, tubes or cuvettes), add an enzyme solution or enzyme-antibody conjugate in solution to each microplate, tubes or cuvettes. Add a solution of D-fructose-1,6-biphosphate, plus MTT, plus PMS. A color indicative of enzymatic activity develops and could be read in a spectrophotometer or plate reader.

EXAMPLE 19

For the study of aldolase inhibition in solution, preincubate the enzyme solution with a solution of inhibitor. Add the substrate solution containing of D-fructose-1,6- biphosphate, MTT and PMS. Observe the development of color as it develops in comparison to a blank solution which contains enzyme and substrate but no inhibitor.

EXAMPLE 20

For phosphoglucomutase detection on a blot assay, the blot could be impregnated with a solution of the enzyme. Allow to dry. Treat the blot with a solution of glucose-1-phosphate, plus MTT, plus PMS. A color indicative of enzymatic activity develops.

EXAMPLE 21

For phosphoglucomutase enzyme detection in solution (microplate, tubes or cuvettes), add an enzyme solution or enzyme-antibody conjugate in solution to each microplate, tubes or cuvettes. Add a solution of glucose-1-phosphate, plus MTT, plus PMS. A color indicative of enzymatic activity develops and could be read in a spectrophotometer or plate reader.

EXAMPLE 22

For the study of phosphoglucomutase inhibition in solution, preincubate the enzyme solution with a solution of inhibitor. Add the substrate solution containing glucose-1-phosphate, MTT and PMS. Observe the development of color as it develops in comparison to a blank solution which contains enzyme and substrate but no inhibitor.

EXAMPLE 23

For DNA ligase enzyme-detection on a blot assay, the blot could be impregnated with a solution of the enzyme. Allow to dry. Treat the blot with a solution of synthetic or natural DNA fragments, plus MTT, plus PMS. A color indicative of enzymatic activity develops.

EXAMPLE 24

For DNA ligase enzyme detection in solution (microplate, tubes or cuvettes), add an enzyme solution or enzyme-antibody conjugate in solution to each microplate, tubes or cuvettes. Add a solution of synthetic or natural DNA fragments, plus MTT, plus PMS. A color indicative of enzymatic activity develops and could be read in a spectrophotometer or plate reader.

EXAMPLE 25

For the study of DNA ligase inhibition in solution, pre-incubate the enzyme solution with a solution of inhibitor. Add the substrate solution containing synthetic or natural DNA fragments, MTT and PMS. Observe the development of color as it develops in comparison to a blank solution which contains enzyme and substrate but no inhibitor.

EXAMPLE 26

For DNA ligase enzyme detection on a blot assay, the blot could be impregnated with a solution of the enzyme. Allow to dry. Treat the blot with a solution of synthetic or natural DNA fragments, plus MTT, plus PMS. A color indicative of enzymatic activity develops.

EXAMPLE 26

For DNA ligase enzyme detection in solution (microplate, tubes or cuvettes), add an enzyme solution or enzyme-antibody conjugate in solution to each tube. Add a solution of synthetic or natural DNA fragments, plus MTT, plus PMS. A color indicative of enzymatic activity develops and could be read in a spectrophotometer or plate reader.

EXAMPLE 27

For the study of DNA ligase inhibition in solution, pre-incubate the enzyme solution with a solution of inhibitor. Add the substrate solution containing synthetic or natural DNA fragments, MTT and PMS. Observe the development of color as it develops in comparison to a blank solution which contains enzyme and substrate but no inhibitor.

The invention has been described with respect to preferred embodiments. However, as those skilled in the art will recognize, modifications and variations in the specific embodiments which have been described and illustrated may be resorted to without departing from the spirit and scope of the invention as defined in the appended claims.

EXAMPLE 28

Microtitre testing was performed with the following substrate combinations, in duplicate, to demonstrate chromogenic detection of acid phosphatase (EC 3.1.3.2)

Reagents:

| | |
|---|---|
| MTT (10 mM) | Dimethylthiazxol Tetrazolium (Sigma M-66H5033) |
| PMS (10 mM) | Phenazine methosulfate (Sigma P-9625) |
| Acid Phosphatase | Sigma (lot #64H7195) solubilized with $H_2O$ (23 units/ml) |
| BCIP | Sigma (B-6274 lot #34H5047) diluted with 2 ml $H_2O$ (12.5 mg/ml) |

Experiment:

| | |
|---|---|
| A. | 100 µl de-ionized $H_2O$ |
| | 10 µl MTT (10 mM) |
| | 10 µl PMS (10 mM) |
| | 10 µl BCIP @ 12.5 mg/ml |
| B. | 100 µl de-ionized $H_2O$ |
| | 10 µl MTT (10 mM) |
| | 10 µl $H_2O$ |
| | 10 µl BCIP @ 12.5 mg/ml |
| C. | 100 µl de-ionized $H_2O$ |
| | 10 µl $H_2O$ |
| | 10 µl PMS (10 mM) |
| | 10 µl BCIP @ 12.5 mg/ml |
| D. | 100 µl de-ionized $H_2O$ |
| | 10 µl MTT (10 mM) |
| | 10 µl PMS (10 mM) |
| | 10 µl BCIP @ 12.5 mg/ml |

5 µl of $H_2O$ was added to substrate sample A as the substrate control. 5 µl of acid phosphatase (0.115U) was added to each substrate samples B, C, D.

Results:

| Sample | Contents | Reaction |
|---|---|---|
| A | MTT, PMS, BCIP | yellow |
| B | MTT, $H_2O$, BCIP | light blue formazan (>5 minutes) |
| C | $H_2O$, PMS, BCIP | faint green detection (3 minutes) |
| D | MTT, PMS, BCIP | dark purple formazan (<1 minute) |

We claim:

1. A method of detecting the presence of chloramphenicol acetyltransferase (CAT) in a test sample, comprising:

combining the test sample with a reagent solution comprising chloramphenicol or a derivative or analog thereof, an acyl CoA compound, and a tetrazolium salt, and wherein the reagent solution does not have an added redox enzyme to create an assay sample; and observing an optical response characteristic of the presence of CAT in the assay sample, thereby detecting the presence of CAT in the test sample.

2. A method according to claim 1, further comprising determining the activity of chloramphenicol acetyltransferase (CAT) in the test sample, by comparing the optical response characteristic of the presence of CAT observed in the assay sample to an optical response characteristic of the presence of CAT obtained from combining one or more standard samples comprising CAT of known activity with one or more reagent solutions comprising chloramphenicol or a derivative or analog thereof, an acyl CoA compound, and a tetrazolium salt, and wherein the reagent solutions do not have an added redox enzyme, and thus determining the activity of CAT in the test sample.

3. A high throughput method of screening test samples for the presence of chloramphenicol acetyl transferase (CAT), comprising:

preparing a plurality of assay samples, each assay sample comprising a test sample and a reagent solution comprising a tetrazolium salt, a chloramphenicol or a derivative or analog thereof, and an acyl CoA compound, and wherein the reagent solution does not have an added redox enzyme, and detecting the presence of CAT in each test sample by observing an optical response characteristic of the presence of CAT in the assay samples which indicates the presence of CAT in the test samples.

4. A high throughput method according to claim 3, further comprising determining the activity of chloramphenicol acetyltransferase (CAT) in the test samples, by comparing the optical response characteristic of the presence of CAT observed in each assay sample to an optical response characteristic of the presence of CAT obtained from combining one or more standard samples comprising CAT of known activity with one or more reagent solutions comprising chloramphenicol or a derivative or analog thereof, an acyl CoA compound and a tetrazolium salt, and wherein the reagent solutions do not have an added redox enzyme, and thus determining the activity of CAT in the test sample.

5. A method according to claims 1, 2, 3, or 4, wherein the optical response is color or fluorescence.

6. A method according to claims 1, 2, 3, or 4, wherein a spectrophotometer or a spectrofluorometer is used to observe the optical response.

7. A method according to claims 1, 2, 3, or 4, wherein the reagent solution further comprises exogenous electron carrier which facilitates the response.

8. A method according to claim 7, wherein the electron carrier is a phenazine salt of the structure:

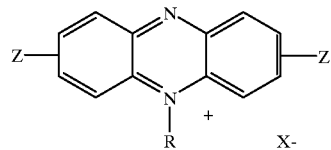

where R is an alkyl, Z is an alkyl, alkoxyl, halo, or nitro, and X is a counter ion.

9. A method according to claim 7, wherein the electron carrier is selected from the group consisting of phenazine methosulfate (PMS) phenazine ethosulfate (PES), nicotinamide adenine dinucleotide (NAD), flavin adenine dinucleotide (FAD) and 4-aminoantipyrine.

10. A method according to claim 9, wherein the electron carrier is phenazine methosulfate (PMS).

11. A method according to claims 1, 2, 3, or 4, wherein the tetrazolium salt has the structure of:

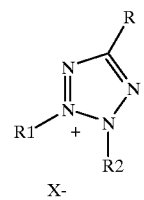

where $R_1$ is aryl or heteroaryl, and $R_2$ is aryl or heteroaryl, and X is a counter ion.

12. A method according to claims 1, 2, 3, or 4, wherein the tetrazolium salt is selected from the group consisting of dimethylthiazolyl tetrazolium (MTT), nitroblue tetrazolium (NBT), 2,3,5-triphenyl tetrazolium chloride (TTC), 2-(2'-benzothiazolyl)-5-stryl-3-(4-phthalhydrazidyl) tetrazolium chloride (BPST), neotetrazolium chloride (NTC), (3,3'-{1-[(phenylamino)carbonyl]-3,4-tetrazolium}-bis(4-methoxy-6-nitro)benzene sulfonic acid) (XTT), p-iodonitrotetrazolium violet (INT) and cyanoditolyl tetrazolium chloride (CTC).

13. A method according to claims 1, 2, 3, or 4, wherein the acyl CoA compound is selected from a group consisting of acyl CoA, acetyl CoA, propionyl CoA, and butyrylCoA.

14. A method according to claims 1, 2, 3, or 4, wherein the test sample is a cell lysate.

15. A method of detecting the expression of a gene of interest by assaying for chloramphenicol acetyltransferase (CAT) present in a sample of a cell lysate due to expression of a CAT gene used as a reporter for measuring expression of a gene of interest in transfected cells, comprising:

combining the test sample with a reagent solution comprising chloramphenicol or a derivative or analog thereof, an acyl CoA compound, and a tetrazolium salt, and wherein the reagent solution does not have an added redox enzyme to create an assay sample; and observing an optical response in the assay sample which is characteristic of the presence of CAT activity, and wherein CAT activity is indicative of the expression of the gene of interest, and thus, upon observation of the optical response characteristic of the presence of CAT activity, detecting the expression of the gene of interest.

16. A method of detecting expression of a gene of interest in transfected cells by measuring the expression of a chloramphenicol acetyltransferase (CAT) gene used as a reporter group, comprising:

combining a sample of cell lysate from the transfected cells with a reagent solution comprising chloramphenicol or a derivative or analog thereof, an acyl CoA compound, and a tetrazolium salt, and wherein the reagent solution does not have an added redox enzyme, to create an assay sample; and measuring an optical response characteristic of the presence of CAT in the assay sample and in samples of CAT of known activity, and wherein CAT activity is indicative of the expression of the gene of interest; and comparing the optical response obtained for the assay sample with the optical response obtained from samples of CAT of known activity to quantitate the expression of the gene of interest.

17. A method according to claims 15 or 16, wherein the optical response is color or fluorescence.

18. A method according to claim 17, wherein a spectrophotometer or a spectrofluorometer is used to observe the optical response.

19. A method according to claims 15 or 16, wherein the reagent solution further comprises an oxogenous electron carrier which facilitates the response.

20. A method according to claim 19, wherein the electron carrier is a phenazine salt.

21. A method according to claim 20, wherein the phenazine salt is phenazine methosulfate (PMS).

22. A method according to claim 19, wherein the electron carrier is a phenazine salt of the structure.

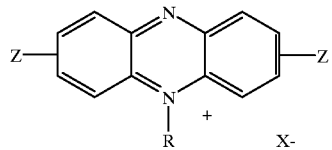

where R is an alkyl, Z is an alkyl, alkoxyl, halo, or nitro, and X is a counter ion.

23. A method according to claim 19, wherein the electron carrier is selected from the group consisting of phenazine methosulfate (PMS) phenazine ethosulfate (PES), nicotinamide adenine dinucleotide (NAD) flavin adenine dinucleotide (FAD) and 4-aminoantipyrine.

24. A method according to claims 15 or 16, wherein the tetrazolium salt has the structure of:

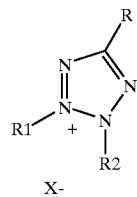

where $R_1$ is aryl or heteroaryl, and $R_2$ is aryl or heteroaryl, and X is a counter ion.

25. A method according to claims 15 or 16, wherein the tetrazolium salt is selected from the group consisting of dimethylthiazolyl tetrazolium (MTT), nitroblue tetrazolium (NBT), 2,3,5-triphenyl tetrazolium chloride (TTC), 2-(2'-benzothiazolyl)-5-stryl-3-(4-phthalhydrazidyl) tetrazolium chloride (BPST), neotetrazolium chloride (NTC), (3,3'-{1-[(phenylamino)carbonyl]-3,4-tetrazolium}-bis(4-methoxy-6-nitro)benzene sulfonic acid) (XTT), p-iodonitrotetrazolium violet (INT) and cyanoditolyl tetrazolium chloride (CTC).

26. A method according to claims 15 or 16, wherein the acyl CoA compound is selected from a group consisting of acyl CoA, acetyl CoA, propionyl CoA, and butyrylCoA.

27. A kit for detecting the presence of chloramphenicol acetyl transferase (CAT), comprising component parts capable of being assembled, comprising:
a tetrazolium salt, chloramphenicol or a derivative or analog thereof, and an acyl CoA salt, and wherein the component parts do not have an added reducing agent.

28. A kit for detecting the presence of chloramphenicol acetyl transferase (CAT), comprising component parts capable of being assembled, comprising:
a tetrazolium salt, chloramphenicol or a derivative or analog thereof, an exogenous electron carrier and an acyl CoA salt, and wherein the component parts do not have an added redox enzyme.

29. A kit for detecting the presence of chloramphenicol acetyl transferase according to claims 27 or 28, wherein the component parts are all contained in a vial or container.

30. A kit for detecting the presence of chloramphenicol acetyl transferase according to claims 27 or 28, wherein the component parts further comprise a reconstitution buffer.

31. A kit for detecting the presence of chloramphenicol acetyl transferase (CAT) in a plurality of test samples having component parts combine of being assembled, comprising a multiplicity of containers, and within each container ingredients comprising a tetrazolium salt, chloramphenicol or a derivative or analog thereof, and an acyl CoA salt, and wherein the containers do not have an added redox enzyme.

32. A kit for detecting the presence of chloramphenicol acetyl transferase (CAT) in a plurality of test samples having component parts combine of being assembled, comprising a multiplicity of containers, each container comprising a tetrazolium salt, chloramphenicol or a derivative or analog thereof, exogenous electron carrier, and an acyl CoA salt, and wherein the containers do not have an added redox enzyme.

33. A kit according to claims 28 or 32, wherein the electron carrier is a phenazine salt.

34. A kit according to claim 33, wherein the phenazine salt is phenazine methosulfate (PMS).

35. A kit according to claim 28 or 32, wherein the electron carrier is a phenazine salt of the structure:

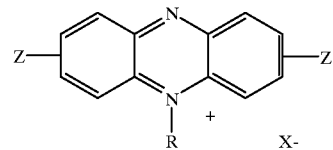

where R is an alkyl, Z is an alkyl, alkoxyl, halo, or nitro, and X is a counter ion.

36. A kit according to claims 27, 28, 31 or 32, wherein the tetrazolium salt has the structure of:

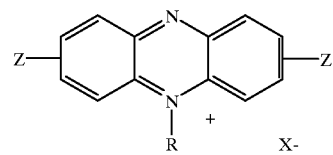

where $R_1$ is aryl or heteroaryl, and $R_2$ is aryl or heteroaryl, and X is a counter ion.

37. A kit according to claims 27, 28, 31 or 32, wherein the tetrazolium salt is selected from the group consisting of dimethylthiazolyl tetrazolium (MTT), nitroblue tetrazolium (NBT), 2,3,5-triphenyl tetrazolium chloride (TTC), 2-(2'-benzothiazolyl)-5-stryl-3-(4-phthalhydrazidyl) tetrazolium chloride (BPST), neotetrazolium chloride (NTC), (3,3'-{1-[(phenylamino)carbonyl]-3,4-tetrazolium}-bis(4-methoxy-6-nitro)benzene sulfonic acid) (XTT), p-iodonitrotetrazolium violet (INT) and cyanoditolyl tetrazolium chloride (CTC).

38. A kit according to claims 27, 28, 31 or 32, wherein the acyl CoA compound is selected from a group consisting of acyl CoA, acetyl CoA, propionyl CoA, and butyrylCoA.

39. A kit according to claims 27, 28, 31 or 32, further comprising a reconstitution buffer.

40. A kit for detecting the presence of chloramphenicol acetyl transferase (CAT), comprising component parts capable of being assembled, consisting essentially of:
   a tetrazolium salt, chloramphenicol or a derivative or analog thereof, and an acyl CoA salt.

41. A kit for detecting the presence of chloramphenicol acetyl transferase (CAT), comprising component parts capable of being assembled, consisting essentially of:
   a tetrazolium salt, chloramphenicol or a derivative or analog thereof, an exogenous electron carrier, and an acyl CoA salt.

42. A kit for detecting the presence of chloramphenicol acetyl transferase (CAT) in a plurality of test samples having component parts capable of being assembled, comprising a multiplicity of containers, each container including components consisting essentially of a tetrazolium salt, chloramphenicol or a derivative or analog thereof, and an acyl CoA salt.

43. A kit for detecting the presence of chloramphenicol acetyl transferase (CAT) in a plurality of test samples having component parts capable of being assembled, comprising a multiplicity of containers, each container including components consisting essentially of a tetrazolium salt, chloramphenicol or a derivative or analog thereof, an exogenous electron carrier and an acyl CoA salt.

44. A kit according to claims 40, 41, 42, or 43, further comprising a reconstitution buffer.

45. A method of detecting the presence of chloramphenicol acetyltransferase (CAT) in a test sample, comprising:
   combining the test sample with a reagent solution consisting essentially of chloramphenicol or a derivative or analog thereof, an acyl CoA compound, and a tetrazolium salt to create an assay sample; and
   observing an optical response characteristic of the presence of CAT in the assay sample, thereby detecting the presence of CAT in the test sample.

46. A method according to claim 45, further comprising determining the activity of chloramphenicol acetyltransferase (CAT) in the test sample, by
   comparing the optical response characteristic of the presence of CAT observed in the assay sample to an optical response characteristic of the presence of CAT obtained from combining one or more standard samples comprising CAT of known activity with one or more reagent solutions consisting essentially of chloramphenicol or a derivative or analog thereof, an acyl CoA compound, and a tetrazolium salt, and
   thus determining the activity of CAT in the test sample.

47. A high throughput method of screening test samples for the presence of chloramphenicol acetyltransferase (CAT), comprising:
   preparing a plurality of assay samples, each assay sample comprising a test sample and a reagent solution consisting essentially of a chloramphenicol or a derivative or analog thereof, an acyl CoA compound, and a tetrazolium salt, and
   detecting the presence of (CAT) in each test sample by observing an optical response characteristic of the presence of CAT in the assay samples which indicates the presence of CAT in the test samples.

48. A high throughput method according to claim 47, further comprising determining the activity of chloramphenicol acetyltransferase (CAT) in the test samples, by
   comparing the optical response characteristic of the presence of CAT observed in the assay sample to an optical response characteristic of the presence of CAT obtained from combining one or more standard samples comprising CAT of known activity with one or more reagent solutions consisting essentially of chloramphenicol or a derivative or analog thereof, an acyl CoA compound, and a tetrazolium salt, and
   thus determining the activity of CAT in the test sample.

49. A method of detecting expression of a gene of interest by assaying for chloramphenicol acetyltransferase (CAT) present in a sample of a cell lysate due to expression of a CAT gene used as a reporter for measuring expression of a gene of interest in transfected cells, comprising:
   combining the sample cell lysate with a reagent solution consisting essentially chloramphenicol or a derivative or analog thereof, an acyl CoA compound, and a tetrazolium salt, to create an assay sample; and
   observing an optical response in the assay sample which is characteristic of the presence of CAT activity, and wherein CAT activity is indicative of the expression of the gene of interest, and thus, upon observation of the optical response characteristic of the presence of CAT activity, detecting the expression of the gene of interest.

50. A method of detecting the presence of chloramphenicol acetyltransferase (CAT) in a test sample, comprising:
   combining the test sample with a reagent solution consisting essentially of chloramphenicol or a derivative or analog thereof, an acyl CoA compound, a tetrazolium salt and a phenazine salt to create an assay sample; and
   observing an optical response characteristic of the presence of CAT in the assay sample, thereby detecting the presence of CAT in the test sample.

51. A method according to claim 50, further comprising determining the activity of chloramphenicol acetyltransferase (CAT) in the test sample, by
   comparing the optical response characteristic of the presence of CAT observed in the assay sample to an optical response characteristic of the presence of CAT obtained from combining one or more standard samples comprising CAT of known activity with one or more reagent solutions consisting essentially of chloramphenicol or a derivative or analog thereof, an acyl CoA compound, and a tetrazolium salt, and a phenazine salt, and
   thus determining the activity of CAT in the test sample.

52. A method of detecting expression of a gene of interest by assaying for chloramphenicol acetyltransferase (CAT) present in a sample of a cell lysate due to expression of a CAT gene used as a reporter for measuring expression of a gene of interest in transfected cells, comprising:
   combining the sample cell lysate with a reagent solution consisting essentially chloramphenicol or a derivative or analog thereof, an acyl CoA compound, and a tetrazolium salt, and a phenazine salt to create an assay sample; and observing an optical response in the assay sample which is characteristic of the presence of CAT activity, and wherein CAT activity is indicative of the expression of the gene of interest, and thus, upon observation of the optical response characteristic of the presence of CAT activity, detecting the expression of the gene of interest.

* * * * *